United States Patent [19]

Hirai et al.

[11] 4,046,785

[45] Sept. 6, 1977

[54] PROCESS FOR PREPARING AMINOANTHRAQUINONES

[75] Inventors: Yutaka Hirai; Katsuharu Miyata; Tagui Osawa; Muneyasu Samecima; Ken Mukai; Koichi Yoshiura; Hidetoshi Mori, all of Ohmuta, Japan

[73] Assignee: Mitsui Toatsu Chemicals, Inc., Tokyo, Japan

[21] Appl. No.: 641,832

[22] Filed: Dec. 18, 1975

[30] Foreign Application Priority Data

Dec. 20, 1974 Japan .................. 49-145615

[51] Int. Cl.$^2$ .................. C09B 1/16; C09B 1/36; C09B 1/50
[52] U.S. Cl. .................. 260/380; 260/377; 260/378
[58] Field of Search .................. 260/380, 378, 377

[56] References Cited

U.S. PATENT DOCUMENTS

| | | | |
|---|---|---|---|
| 1,957,920 | 5/1934 | Whelen | 260/380 X |
| 1,957,936 | 5/1934 | Buxbaum | 260/380 X |
| 2,653,954 | 9/1953 | Weinmayr | 260/380 |
| 3,060,200 | 10/1962 | Buecheler | 260/380 |

OTHER PUBLICATIONS

House, "Modern Synthetic Reaction", 2nd Ed., W. A. Benjamin, Inc., Menlo Park, Cal. (1972), pp. 1–10 and 210.

*Primary Examiner*—Paul F. Shaver
*Attorney, Agent, or Firm*—Sherman & Shalloway

[57] ABSTRACT

A process for preparing aminoanthraquinones of high purity, which comprises catalytically hydrogenating nitroanthraquinones in the suspended state in an aqueous medium in the presence of a hydrogenating catalyst. In a preferred embodiment, the catalytic hydrogenation may be carried out in the presence of an organic or inorganic base, followed, if desired, by oxidizing the hydrogenation product.

9 Claims, No Drawings

PROCESS FOR PREPARING AMINOANTHRAQUINONES

This invention relates to a process for preparing aminoanthraquinones.

Aminoanthraquinones are important intermediates for disperse dyes, vat dyes and pigments. They are presently synthesized by reducing nitroanthraquinones with a reducing agent such as an alkali sulfide, an alkali hydrosulfide or an alkali polysulfide in an aqueous medium. However, the use of sulfide compounds as a reducing agent has imposed a considerable restriction on the performance of this process in view of its adverse effects on the working environment and on the control of environmental pollution.

Generally, nitro compounds are reduced effectively by catalytic hydrogenation, and this technique has gained wide commercial acceptance. In spite of this, catalytic hydrogenation has scarcely been utilized for the reduction of nitroanthraquinones, and the only pertinent literature reference we know is V. M. Chursina, Izv. Akad, Nauk, SSSR, Ser. Khim., 1969, page 2550 which discloses the hydrogenation of nitroanthraquinones in a sulfuric acid solvent using a palladium catalyst. The main reasons for this are cited below.

Since nitroanthraquinones as raw materials and aminoanthraquinones as reduction products are only sparingly soluble in common organic solvents the reaction mixture becomes slurry-like, and this causes difficulties in performing the reaction. The catalyst and the reaction product are difficult to separate from each other. Furthermore, during the hydrogenation reaction, the hydrogenation of a carbonyl group on the anthraquinone nucleus and of the nucleus itself tends to occur in addition to the reduction of the nitro group. This results in the formation of various by-products such as 1-aminoanthrahydroquinone, 1-aminoanthranol, 1-amino-5,6,7,8-tetrahydroanthraquinone, and 1-amino-1,2,3,4,5,6,7,8-octahydroanthraquinone, and deteriorates the quality of the product.

Sulfuric acid is a solvent which can dissolve aminoanthraquinones relatively easily. In the Chursina's method described above in which hydrogenation is carried out using sulfuric acid, the reaction is so slow that very large quantities of catalyst are required. Also, various by-products are formed in large quantities.

We previously found that carboxylic acid amides can dissolve aminoanthraquinones more easily than other solvents. But we ascertained that when, for example, N,N-dimethyl formamide is used as a solvent in the hydrogenation of nitroanthraquinones, the reaction is rapid, but because of the formation of unidentified substances in addition to the corresponding aminoanthraquinones, the product cannot be used directly as dyes or pigments. Thus, we regard carboxylic acid amides as unsuitable hydrogenation solvents.

Accordingly, it is an object of this invention to provide a process for preparing aminoanthraquinones by catalytic hydrogenation of nitroanthraquinones without involving the above-mentioned drawbacks.

It has not been found that when an aqueous medium i.e. water or a mixture of water and an organic solvent, is used as a reaction medium, the reduction of nitroanthraquinones proceeds in the suspended state, and the resulting aminoanthraquinones have better quality with lesser amounts of impurities than in the case of using an organic solvent as the reaction medium.

According to this invention, there is provided a process for preparing aminoanthraquinones, which comprises catalytically hydrogenating a nitroanthraquinone of the general formula

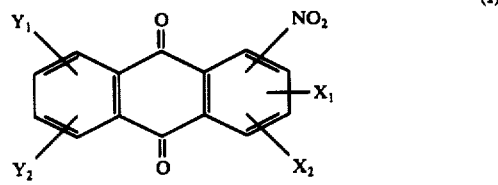

wherein $X_1$ represents a hydrogen atom, a helogen atom, a lower alkyl group, a lower alkoxy group, a carboxyl group or a phenoxy group whose benzene nucleus optionally contains a substituent, $X_2$ represents a hydrogen atom, a hydroxyl group or an amino group, and $Y_1$ and $Y_2$, independently from each other, represent a hydrogen atom, a halogen atom, a nitro group, an amino group, a hydroxyl group, a lower alkyl group, a lower alkoxy group or a phenoxy group whose benzene nucleus optionally contains a substituent, with the proviso that when the nitro group is bonded to the 1-position, $X_1$, $X_2$, $Y_1$ and $Y_2$ do not at the same time represent a hydrogen atom, in the suspended state in an aqueous medium in the presence of a hydrogenating catalyst.

In the process of this invention, the reaction proceeds while the reaction mixture is in the form of slurry. Accordingly, when particles having a particle size above a certain limit or not readily disintegratable masses exist in the starting nitroanthraquinone, it sometimes happens that only the surfaces of the particles or masses react, and their inside remains unreacted or becomes a reaction intermediate. Consequently, the reaction stops halfways, and may exert adverse effects on the quality and yield of the final product. Accordingly, it is preferred to use the nitroanthraquinone after pulverizing it to a particle size below a certain limit. This permits faster rates of reaction and smoother progress of the reaction than in the case of using unpulverized raw materials, and the corresponding aminoanthraquinones of good quality can be stably produced without leaving the unreacted matter or the intermediate.

The nitroanthraquinone can be finely divided by conventional pulverizing means such as a stone ball mill, ball mill, rod mill, hammer mill, colloid mill, roller mill, attriter or sand grinder. This pulverization can also be carried out during the progress of the reaction of the nitroanthraquinone, in which case the purpose of pulverization can be achieved, for example, by placing balls of suitable material and size in a reactor of a suitable structure. The use of a dispersing agent which does not adversely affect the hydrogenation reaction is effective, but not always essential.

In most cases, nitroanthraquinones prepared by customary methods contain at least 10% of particles with a size of at least 100 microns. When they are used as starting materials in the process of this invention, they can be pulverized by the above methods to such an extent that at least 95% of the entire particles have a size of not more than 30 microns. When at least 95% of the entire particles have a size of not more than 30 microns, the hydrogenation reaction proceeds smoothly, and the corresponding aminoanthraquinones of good quality can be obtained.

The aminoanthraquinone obtained as a reaction product is scarcely soluble in the aqueous medium, but precipitates. Accordingly, it is withdrawn together with the catalyst, and dissolved in a solvent such as sulfuric acid or an organic solvent to separate the catalyst. At the time of separating the catalyst, impurities contained in the aminoanthraquinone can also be removed.

In a preferred embodiment of this invention, aminoanthraquinones of good quality can be obtained in high yields by hydrogenating a nitroanthraquinone of formula (I) in an aqueous medium in the presence of a base using an ordinary hydrogenating catalyst, and if desired oxidizing the resulting hydrogenated product with a suitable oxidizing agent such as air or hydrogen peroxide. When the hydrogenation is carried out in the presence of bases, the nitro group is reduced to an amino group to form an aminoanthraquinone which then undergoes hydrogenation to form a salt of a hydroquinone compound of the aminoanthraquinone.

In the process of this invention, the nitroanthraquinones of general formula (I) are used either alone or as mixtures. In formula (I), the lower alkyl group and the lower alkoxy group are straight-chain or branched-chain alkyl and alkoxy groups containing 1 to 4 carbon atoms which may be substituted by a hydroxyl group or a lower alkoxy group with up to 4 carbon atoms. Suitable halogen atoms are chlorine and bromine. When $X_1$, $X_2$, $Y_1$ or $Y_2$ represents a phenoxy group, it may be substituted by a hydroxyl group, a halogen atom, a nitro group, a straight-chain or branched-chain alkoxy group with up to 4 carbon atoms, or a straight-chain or branched-chain alkyl group with up to 4 carbon atoms.

Specific examples of the nitroanthraquinones of formula (I) are 2-nitroanthraquinone, 1,5-, 1,8-, 1,6- or 1,7-dinitroanthraquinone, 1-nitro-2-methylanthraquinone, 1-nitro-2-chloroanthraquinone, 1-nitro-2-carboxyanthraquinone, 1,5-dinitro-4,8-dihydroxyanthraquinone, 1,8-dinitro-4,5-dihydroxyanthraquinone, 1,5-dinitro-4,8-dimethoxyanthraquinone, 1,8-dinitro-4,5-dimethoxyanthraquinone, 1,5-dinitro-4,8-dimethoxy-3-bromoanthraquinone, 1,5-dinitro-4,8-dihydroxy-3-bromoanthraquinone, 1,5-dinitro-4,8-di(2',4'-dinitrophenoxy) anthraquinone, 1,4-diamino-5-nitroanthraquinone, 1,4,5-trinitro-8-hydroxyanthraquinone, 1,4,5-trinitro-8-methoxyanthraquinone, 1,4,5-trihydroxy-8-nitroanthraquinone, 1,5-dinitro-4,8-dichloroanthraquinone, 1,8-dinitro-4,5-dichloroanthraquinone, 1-chloro-5-nitroanthraquinone, 1,5-dinitro-2-methylanthraquinone, 1,5-dinitro-4,8-diaminoanthraquinone, 1,8-dinitro-4,5-diaminoanthraquinone, 1-nitro-4,5-dihydroxyanthraquinone, 1-nitro-4,8-dihydroxyanthraquinone, 1-nitro-4,5-dimethoxyanthraquinone, 1-nitro-4,8-dimethoxyanthraquinone, 1-amino-2-carboxy-4-nitroanthraquinone, 2-chloro-5-nitroanthraquinone, 2-chloro-8-nitroanthraquinone, 2,3-dichloro-5-nitroanthraquinone, 1,4-dichloro-5-nitroanthraquinone, 1,5,8-trichloro-4-nitroanthraquionone, 2-bromo-5-nitroanthraquinone, 1,4-dibromo-5-nitroanthraquinone, 2-chloro-1,5-dinitroanthraquinone, and 2-chloro-1,8-dinitroanthraquinone.

The hydrogenation in the process of this invention can be carried out at atmospheric pressure or at an elevated pressure. For example, according to the atmospheric pressure method, a reactor equipped with a stirrer and a hydrogen-introducing tube is charged with the starting material, an aqueous medium and a catalyst with or without the addition of an inorganic or organic base, and the reaction is carried out with stirring at a predetermined temperature while introducing hydrogen. According to the elevated pressure process, these materials are placed in a pressure reactor, and reacted with stirring or shaking while introducing hydrogen under pressure. A continuous reaction process can also be utilized in the present invention.

When water is used as the aqueous medium, its suitable amount is 5 to 200 times, preferably 10 to 60 times, the weight of the starting nitroanthraquinone. An organic solvent can be used together with water. The organic solvent should be inert to the reaction system, and examples include aromatic hydrocarbons whose aromatic nucleus is optionally substituted by one to several halogen atoms; aliphatic, araliphatic and cycloaliphatic hydrocarbons containing 5 to 12 carbon atoms; halogenated aliphatic hydrocarbons containing 1 to 6 carbon atoms which are substituted by one to several halogen atoms; ethers such as anisole, dialkyl ethers, tetrahydrofuran, or dioxane; aliphatic and cycloaliphatic ketones such as acetone, methyl ethyl ketone or cyclohexanone; and mono- or polyhydric aliphatic and cycloaliphatic alcohols containing 1 to 6 carbon atoms.

When the organic solvent is used together with water, it can be added before or during the hydrogenating reaction. When the organic solvent is used together, the post-treatment of the product (the removal of insoluble matter and oxidation) subsequent to the end of the hydrogenation reaction can be performed after recovering the organic solvent or without recovering it.

The suitable amount of the organic solvent is up to 50 times, preferably not more than 20 times, the weight of nitroanthraquinone. The organic solvent forms an aqueous medium by being mixed with water in the above-mentioned amount. The proportion of the organic solvent in the aqueous medium is generally not more than 50% by weight, preferably not more than 30% by weight.

By using the organic solvent together, the properties of the interface between the reaction medium and the suspended materials change, and therefore, favorable results are brought about. For example, the reaction can be performed while maintaining the concentration of the slurry high, and moreover, the rate of reaction is somewhat increased.

When the starting nitroanthraquinone contains an organic solvent entrained during its production process, it is not necessary to remove the organic solvent prior to use in the process of this invention. But usually, the hydrogenation reaction can be carried out using only water as a reaction medium, and no organic solvent is required. The reaction is carried out usually in suspension. But in order to facilitate the progress of reaction, a surface active agent that does not adversely affect the hydrogenation reaction can also be used. Examples of suitable surface active agents are nonionic surface active agents such as polyoxyethylene alkyl ethers or polyoxyethylene alkylaryl ethers, and anionic surface active agents such as alkylarylsulfonic acids. The amount of the surface active agent is 0.001 to 1.0 time, preferably 0.005 to 0.5 time, the weight of the nitroanthraquinone.

The addition of a surface active agent changes the properties of the interface between the reaction medium and the suspended materials, and brings about favorable results. For example, the reaction can be performed while maintaining the concentration of the slurry high, and the reaction mixture can be stirred easily. Moreover, the rate of reaction is somewhat increased. Generally, however, the reaction can be carried out satisfactorily without using surface active agents.

There is no particular restriction on the inorganic or organic bases that can be used in the process of this invention. Examples of suitable bases are hydroxides, carbonates, acetates and phosphates of alkali metals or alkaline earth metals such as sodium, potassium, calcium, barium or magnesium, ammonia, diethylamine, morpholine, piperidine, ethanolamine, piperazine, ethylenediamine, 1,4-diazabicyclooctane, and 1,7-diazaundecene. These bases can be used either alone or as mixtures. The suitable amount of the base is at least 1 mole, preferably 1 to 20 moles, per mole of the nitroanthraquinone of formula (I). Preferably, the base is added at the outset of the hydrogenation reaction, but a part or the whole of it may be added during the reaction.

The hydrogenating catalyst used in the process of this invention may be any hydrogenating catalysts usually employed for converting nitro compounds to amino compounds by catalytic hydrogenation. Examples include catalysts containing a metal such as palladium, platinum, ruthenium, rhodium, nickel, cobalt or copper as an active ingredient. Palladium catalysts supported on a carrier such as carbon, alumina, diatomaceous earth, or silica gel are especially suitable. The amount of the catalyst differs according to the reaction conditions and the type of the catalyst. But when the reaction is carried out using a supported palladium catalyst, the suitable amount of the catalyst is 0.01 to 1.0 parts by weight, as palladium metal, per 100 parts by weight of the starting materials. When the catalyst is used without a carrier, for example, in the case of palladium black, the suitable amount of the catalyst is 0.01 to 5.0 parts by weight per 100 parts by weight of the starting material.

The reaction temperature that can be used in this invention is 0° to 160° C., preferably 10° to 80° C., more preferably 15° to 60° C., and the reaction pressure is preferably from atmospheric pressure to 100 Kg/cm². The reaction in accordance with this invention, however, proceeds even at room temperature and atmospheric pressure. When the reaction temperature is too high, undesirable by-products are liable to be formed.

The reaction product after the end of the hydrogenation, if desired, is treated with an oxidizing agent. Examples of the oxidizing agent that can be used in this invention are air, oxygen, hydrogen peroxide, sodium peroxide, perborates, peroxides of organic acids or salts thereof, peroxides of orgaic acid anhydrides, persulfates, hypochlorites, bleaching powder, and chlorine. Of these, air is especially preferred. For example, by passing air into the reaction mixture at a temperature of 0° to 120° C., preferably 10° to 80° C., the oxidation of the reaction product is effected. The time required for the oxidation is 0.5 to 10 hours, 0.5 to 5 hours under preferred conditions, and less than 0.5 hour under more preferred conditions. The aminoanthrahydroquinone dissolved as a soluble salt is converted to an aminoanthraquinone by the oxidation, and precipitates from the aqueous medium.

The reaction product is then filtered to collect a mixture of the catalyst and the resulting aminoanthraquinone. The aminoanthraquinone is separated from this mixture using a solvent that can readily dissolve aminoanthraquinones. Examples of suitable solvents for this purpose include aliphatic glycols such as ethylene glycol, propylene glycol, diethylene glycol and dipropylene glycol; alicyclic alcohols such as cyclohexanol and methyl cyclohexanol; carboxylic acid amides such as N,N-dimethyl formamide, N,N-dimethyl acetamide and N-methyl-2-pyrrolidone; ethers such as dioxane, tetrahydrofuran and methoxybenzene; substituted aromatic hydrocarbons such as toluene, xylene, chlorobenzene and dichlorobenzene; ether alcohols such as methoxyethanol; sulfuric acid; and dimethyl sulfoxide. The aminoanthraquinone solution separated from the catalyst is either cooled, diluted with a solvent which sparingly dissolves aminoanthraquinones (such as water), or concentrated, thereby to recover the aminoanthraquinone efficiently.

When the hydrogenation is carried out using an alkali metal or alkaline earth metal hydroxide, such as sodium hydroxide or potassium hydroxide, as the base in an amount of at least 2/n (n being the atomic valency of the alkali metal or alkaline earth metal) moles per mole of the nitroanthraquinone of formula (I), the reaction mixture generally dissolves as a salt of an aminoanthrahydroquinone corresponding to the starting material of formula (I). Accordingly, the catalyst can be separated without using an organic solvent. Separation of the catalyst can usually be effected in an atmosphere of air, but preferably in an atmosphere of an inert gas such as nitrogen. If desired, the filtrate left after the separation of the catalyst is oxidized with an oxidizing agent such as air or hydrogen peroxide to afford an aminoanthraquinone corresponding to the starting material of formula (I) with good efficiency.

Where the nitroanthraquinone of formula (I) contains a carboxyl or hydroxyl group as a substituent, the resulting aminoanthraquinone sometimes dissolves in the aqueous medium. In such a case, it is not necessary to reduce the aminoanthraquinone to aminoanthrahydroquinone, and therefore, the catalyst can be separated at a stage where the aminoanthraquinone is formed. In this case, the filtrate left after the separation of the catalyst is neutralized with a mineral acid such as sulfuric acid, hydrochloric acid or phosphoric acid or an organic acid such as acetic whereby the desired aminoanthraquinone is freed and precipitated.

According to the process of this invention, the reaction can be controlled by the amount of hydrogen required to convert the nitroanthraquinone of formula (I) to its corresponding aminoanthraquinone or its aminoanthrahydroquinone. The process of this invention makes it possible to prepare aminoanthraquinones important as dye intermediates with commercial simplicity by using an aqueous medium, and is advantageous from the standpoint of safety and control of environmental pollution. The aminoanthraquinones obtained by the process of this invention have good quality, and are sufficiently feasible as dye intermediates.

The following Examples illustrate the present invention more specifically.

EXAMPLE 1

A 500 ml. electromagnetically stirred glass reactor was charged with 5.0 g (0.0167 mole) of dinitroanthraquinone (a mixture of 1,5-isomer and 1,8-isomer), 100 g (0.1 mole) of a 4% aqueous solution of sodium hydroxide and 0.25 g of 5% palladium-carbon. The inside of the reactor was purged with hydrogen, and the dinitroanthraquinone was hydrogenated at 30° C. with stirring. In 5 hours, 0.1169 mole of hydrogen was absorbed, the reaction was stopped. The reaction mixture was filtered in an atmosphere of nitrogen to separate the catalyst. Then, the filtrate was oxidized with air with stirring at 20° to 30° C. for 2 hours. The resulting crystals were filtered and dried to afford 3.9 g of diaminoanthraquinone (a mixture of 1,5-isomer and 1,8-isomer) in a yield of 97.5%.

When the above procedure was repeated except that 30% hydrogen peroxide, a 15% aqueous solution of sodium hypochlorite or sodium perborate was used instead of the air in the oxidation treatment, the same results were obtained.

EXAMPLE 2

In the same way as in Example 1, the hydrogenation was carried out for 5 hours using 100 g of water and 10 g of dipropylene glycol instead of 100 g of the 4% aqueous solution of sodium hydroxide. When the amount of hydrogen absorbed reached 0.1002 mole, the reaction was stopped. The reaction product was filtered. 40 g of 98% sulfuric acid was added to the filtrate mass, and the catalyst was separated by filtration. The filtrate was then poured into water. The crystals precipitated were filtered, washed with water, and dried to afford 3.9 g of diaminoanthraquinone (a mixture of 1,5-isomer and 1,8-isomer) in a yield of 97.5%.

EXAMPLE 3

A 500 ml. electromagnetically stirred glass reactor was charged with 5.0 g (0.0168 mole) of 1-nitro-2-carboxyanthraquinone, 100 g of a 4% aqueous solution of sodium hydroxide and 0.25 g of 5% palladium-carbon. The inside of the reactor was purged with hydrogen, and the 1-nitro-2-carboxyanthraquinone was hydrogenated at 50° C. with stirring. In 5 hours, 0.0504 mole of hydrogen was absorbed, whereupon the reaction was stopped. The reaction mixture was filtered to separate the catalyst. The filtrate was oxidized with air with stirring at 20° to 30° C. for 2 hours, and then neutralized with 20% sulfuric acid to a pH of 2 to 3. The crystals precipitated were filtered, washed with water, and dried to afford 4.1 g of 1-amino-2-carboxyanthraquinone in a yield of 91.3%.

EXAMPLE 4

A 500 ml. electromagnetically stirred glass reactor was charged with 5.0 g (0.0151 mole) of 1,5-dinitro-4,8-dihydroxyanthraquinone, 100 g of a 4% aqueous solution of sodium hydroxide and 0.25 g of 5% palladium-carbon. The inside of the reactor was purged with hydrogen, and the 1,5-dinitro-4,8-dihydroxyanthraquinone was hydrogenated at 50° C. with stirring. In 5 hours, 0.0906 mole of hydrogen was absorbed, whereupon the reaction was stopped. The reaction mixture was filtered to separate the catalyst. The filtrate was oxidized with air with stirring at 20° to 30° C. for 2 hours, and then neutralized with 20% sulfuric acid to a pH of 2-3. The crystals precipitated were filtered, washed with water, and dried to afford 4.0 g of 1,5-diamino-4,8-dihydroxyanthraquinone in a yield of 97.8%.

EXAMPLE 5

A 160 ml. electromagnetically stirred autoclave was charged with 2.53 g (0.01 mole) of 2-nitroanthraquinone, 52 g (0.052 mole) of a 4% aqueous solution of sodium hydroxide, and 0.07 g of Raney nickel, and the 2-nitroanthraquinone was hydrogenated at room temperature and a pressure of 6 to 3 Kg/cm$^2$.G with stirring. The reaction was stopped in 6 hours with the absorption of 0.04 mole of hydrogen. The inside of the reactor was purged with nitrogen, and the reaction mixture was filtered in a stream of nitrogen to separate the catalyst. The filtrate was oxidized with air with stirring at 20° to 30° C. for 2 hours to afford 2.1 g of high purity 2-aminoanthraquinone.

EXAMPLE 6

2.5 g (0.01 mole) of 2-nitroanthraquinone (purity above 99%) containing about 10% of particles having a particle diameter of more than 100 microns was placed in a 200 ml. electromagnetically stirred autoclave together with 25 g of small glass balls each with a diameter of 1 mm, 75 g of water and 0.025 g of 5% palladium-carbon. The inside of the autoclave was purged with hydrogen, and then, the 2-nitroanthraquinone was hydrogenated with stirring at a temperature of 100° C. and a pressure of 2 to 6 Kg/cm$^2$.G. The reaction proceeded smoothly, and stopped in 4 hours with the absorption of a theoretical amount of hydrogen. The reaction mixture was filtered, and the 22 g of conc. sulfuric acid was added to the filtrate mass to dissolve the reaction product. Then, the catalyst and the small glass balls were separated by filtration. The filtrate was diluted with water. The precipitated crystals were collected by filtration to afford 2.2 g of 2-aminoanthraquinone. The purity of the product was 99%, and its yield was almost quantitative.

EXAMPLE 7

A 500 ml. electromagnetically stirred glass reactor was charged with 5.0 g of dinitroanthraquinone (a mixture of 1,5-isomer and 1,8-isomer), 50 g of a 4% aqueous solution of sodium hydroxide, 50 g of toluene and 0.25 g of 5% palladium-carbon, and the dinitroanthraquinone was hydrogenated with stirring at a pressure of 40 to 30 Kg/cm$^2$.G and a temperature of 40° to 50° C. The reaction was stopped in 5 hours with the absorption of 0.1169 mole of hydrogen. 50 g of a 4% aqueous solution of sodium hydroxide was added, and the reaction mixture was filtered in a stream of nitrogen to separate the catalyst. The filtrate was separated into an aqueous pahse and a toluene phase. The aqueous phase was oxidized with air with stirring at 20° to 30° C. for 2 hours. The crystals precipitated were filtered and dried to afford 3.9 g of diaminoanthraquinone in a yield of 97.5%.

When the above procedure was repeated using benzene or cyclohexane instead of the toluene, the same results were obtained.

What we claim is:

1. A process for preparing aminoanthraquinones, which comprises catalytically hydrogenating a nitroanthraquinone of the general formula

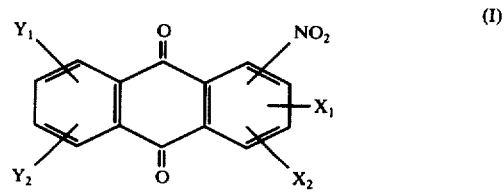

(I)

wherein X$_1$ represents a hydrogen atom, a halogen atom, a lower alkyl group, a lower alkoxy group, a carboxyl group or a phenoxy group whose benzene nucleus optionally contains a substituent, X$_2$ represents a hydrogen atom, a hydroxyl group or an amino group, and $Y_1$ and $Y_2$, independently from each other, represent a hydrogen atom, a halogen atom, a nitro group, an amino group, a hydroxyl group, a lower alkyl group, a lower alkoxy group or a phenoxy group whose benzene nucleus optionally contains a substituent, with the proviso that when the nitro group is bonded to the 1-position, $X_1$, $X_2$, $Y_1$ and $Y_2$ do not at the same time represent a hydrogen atom, in the suspended state in an aqueous medium in the presence of a hydrogenating catalyst.

2. The process of claim 1 wherein said catalytic hydrogenation is carried out after pulverizing the nitroanthraquinone of formula (I) or while pulverizing it.

3. The process of claim 1 wherein said catalytic hydrogenation is carried out in the presence of an inorganic or organic base.

4. The process of claim 1 wherein an alkali metal or alkaline earth metal hydroxide is added in an amount of at least 2/n moles, n being the atomic valency of the alkali metal or alkaline earth metal, per mole of the nitroanthraquinone of formula (I) at the outset of, or during, the catalytic hydrogenation to form a soluble salt of an aminoanthraquinone corresponding to the compound of formula (I) or an aminoanthrahydroquinone, and then the catalyst is separated.

5. The process of claim 1 wherein the aqueous medium is water.

6. The process of claim 1 wherein the aqueous medium is a mixture of water and an organic solvent, the latter being present in a proportion of not more than 50% by weight of the entire mixture.

7. The process of claim 6 wherein the organic solvent is selected from the group consisting of aromatic hydrocarbons optionally substituted by one to several halogen atoms, aliphatic, araliphatic and cycloaliphatic hydrocarbons containing 5 to 12 carbon atoms, halogenated aliphatic hydrocarbons containing 1 to 6 carbon atoms and substituted by one to several halogen atoms, ethers selected from the group consisting of anisole, dialkyl ethers, tetrahydrofuran and dioxane, aliphatic and cycloaliphatic ketones selected from the group consisting of acetone, methyl ethyl ketone and cyclohexanone, and mono- or polyvalent aliphatic and cycloaliphatic alcohols containing 1 to 6 carbon atoms.

8. The process of claim 1 wherein the nitroanthraquinone of formula (I) is selected from the group consisting of 1,5-dinitroanthraquinone, 1,8-dinitroanthraquinone, 1-nitro-2-carboxyanthraquinone, 1,5-dinitro-4,8-dihydroxyanthraquinone, 1,8-dinitro-4,5-dihydroxyanthraquinone, 1,5-dinitro-4,8-dimethoxyanthraquinone, and 2-nitroanthraquinone, and mixtures thereof.

9. The process of claim 3 which further comprises oxidizing said hydrogenation product.

* * * * *